United States Patent [19]

Schultz et al.

[11] Patent Number: 5,199,954
[45] Date of Patent: Apr. 6, 1993

[54] HAIR COLORING DYES INCORPORATING ARYL AMINES AND ARYL ALDEHYDES

[75] Inventors: Thomas M. Schultz, Ridgefield, Conn.; Catherine Grillo, Nyack, N.Y.; Sanae Kubo, Darien, Conn.

[73] Assignee: Shiseido Co., Ltd., Tokyo, Japan

[21] Appl. No.: 840,522

[22] Filed: Feb. 25, 1992

[51] Int. Cl.$^5$ ............................................. A61K 7/13
[52] U.S. Cl. .................................... 8/408; 8/406; 8/409; 8/410; 8/415; 8/416; 8/423; 8/424; 8/429; 8/613; 8/621; 8/624; 8/634; 424/70
[58] Field of Search .................. 8/405, 406, 408, 409, 8/410, 415, 416, 423, 424, 429, 613, 621, 624, 634; 424/70

[56] References Cited

U.S. PATENT DOCUMENTS

| | | | |
|---|---|---|---|
| 3,918,896 | 11/1975 | Kalopissis et al. | 8/408 |
| 4,391,603 | 7/1983 | Rosenbaum et al. | 8/405 |
| 4,466,805 | 8/1984 | Welters et al. | 8/408 |
| 4,775,526 | 10/1988 | Lang et al. | 8/405 |
| 4,828,568 | 5/1989 | Konrad et al. | 8/408 |
| 4,932,977 | 7/1990 | Schultz | 8/408 |
| 4,946,472 | 8/1990 | Motono | 8/405 |
| 4,981,485 | 1/1991 | Motono | 8/405 |
| 4,992,077 | 2/1991 | Tennigkeit et al. | 8/405 |
| 5,034,014 | 7/1991 | Wenke | 8/410 |
| 5,078,750 | 1/1992 | Komai et al. | 8/405 |

Primary Examiner—Paul Lieberman
Assistant Examiner—William S. Parks
Attorney, Agent, or Firm—Melvin I. Stoltz

[57] ABSTRACT

An easily employed, effective and predictable hair dye composition is obtained by combining aryl amines with aryl aldehydes along with an inorganic metal salt having a valence between +1 and +3. By employing this formulation, a permanent, long-lasting, non-fading hair coloring is achieved. In the preferred embodiment, the inorganic metal salt is selected from the group consisting of aluminum chloride, ferric chloride, lithium bromide, manganese chloride, copper chloride, and manganese nitrate. In carrying out the teaching of the present invention, the aryl amine and aryl aldehyde may be applied to the hair separately or in combination, along with the inorganic metal salt. In addition, this inorganic metal salt can be applied after the application and removal of the aryl amine and aryl aldehyde.

9 Claims, No Drawings

HAIR COLORING DYES INCORPORATING ARYL AMINES AND ARYL ALDEHYDES

TECHNICAL FIELD

This invention relates to dye compositions for coloring human hair and, more particularly, to hair coloring dyes incorporating aryl amines and aryl aldehydes.

BACKGROUND ART

Throughout the years, there has been a desire to alter the color of human hair in view of changing styles and fashion. However, due to the inherent composition of hair fiber, and the chemical and mechanical exposure encountered by the hair fibers during normal care and styling, obtaining and maintaining a precise color has been an illusive goal.

As is well known, hair is composed of a unique protein material called "keratin" which is repeatedly being subjected to both chemical and mechanical damage from combing and brushing, as well as from sunlight, chlorinated water, shampooing, permanent waving and other such treatments involving various chemicals. As a result, depending upon the length of the hair fiber, the distal ends of each hair fiber tend to have substantially more damage than the proximal ends nearer to the scalp. This inconsistency causes variation in the dye uptake by the hair fiber, resulting in color variations along the length of the hair fiber.

In spite of the long history associated with the coloration of hair and the extensive effort that has been expended in attempting to eliminate the problems associate with the dyeing of human hair, no system has been achieved which is capable of overcoming all of the drawbacks and difficulties encountered with hair dyes. Included among these drawbacks is the need for a dye system which avoids any adverse effect on the skin on the hair of the user.

In addition, the longevity of the resulting dye, its ability to resist fading, and its ability to resist color changes due to washing, combing, or rubbing, represent other problems which continue to plague conventional prior art dyes. Furthermore, the accuracy of the color imparted to the hair fiber during the dyeing process, as well as the ease with which the hair fiber is capable of being dyed, are also important factors which prior are dye compositions have been incapable of successfully overcoming.

For many years, the dyes employed with fabrics, such as wool or cotton, have been mixed with mordanting solutions in order to prevent or reduce light-induced fading of the dyed material. However, no comparable solution has been realized in prior art hair dye compositions.

In spite of the numerous attempt and extensive effort that has been expended through the long history of dye use and formulations of prior art compositions, no commercially successful hair dye product has been achieved which is capable of providing a universally applicable, commercially acceptable product which overcomes all of the prior art drawbacks. In addition, the prior art dye systems have often proven to be expensive, with only limited or partial success.

Therefore, it is a principal object of the present invention to provide a dye composition for use on human hair which is capable of being easily and successfully employed on all hair fibers with consistent, repeatable and predictable hair coloration results.

Another object of the present invention is to provide a dye composition for use of human hair having the characteristic features described above which substantially reduces and virtually eliminates any irritation that may result to the skin of the user.

Another object of the present invention is to provide a dye composition for use on human hair the characteristic features described above which can be formulated for achieving virtually and desired hair coloration.

Other and more specific objects will apart be obvious and will in part appear hereinafter.

DETAILED DESCRIPTION

In the present invention, most of the prior art failings and drawbacks have been overcome and an effective, predictable, easily employed hair dye composition has been realized. In this invention, aryl amines and aryl aldehydes have been combined to provide stable, long-lasting hair dye compositions. Prior to this invention, colors formed from chemical reactions of an aryl amine and an aryl aldehyde have generally produced hair dye compositions which are unstable when exposed to light or are unstable when contacted with dilute alkaline solutions. However, in the present invention, all of these prior art inabilities have been overcome.

In the hair dye composition of the present invention, a stable, effective hair dye composition is obtained by combining an aryl amine and an aryl aldehyde and intermixing this combination with an inorganic metal salt having a valence between $+1$ and $+3$. By incorporating an inorganic metal salt, which functions as a Lewis Acid, the aryl amine and the aryl aldehyde combination produce substantive, predictable, long-lasting coloring to the hair.

In employing the present invention, it has been found that the inorganic metal salt is preferably selected from the group consisting of aluminum chloride, ferric chloride, lithium bromide, manganese chloride, copper chloride, and manganese nitrate. Although theses inorganic metal salts are preferred, it has been found that any inorganic metal salt having a valence of between $+1$ and $+3$ are effective in providing a hair dye composition of the present invention.

In addition to the preferred inorganic metal salts employed in the hair dye composition of this invention, the preferred aryl amine comprises one selected from the group consisting of p-phenylenediamine, N-phenyl-p-phenylenediamine, p-aminophenol and N,N-bishydroxyethyl-p-phenylenediamine. Although any desired aryl aldehyde can also be employed, it has been found that the preferred aryl aldehyde is selected from the group consisting of N,N-dimethyl-4-aminobenzaldehyde, N,N-dimethyl-4-aminocinnamaldhyde, 3,4-dihydroxybenzaldehyde, 2,4-dihydroxybenzaldehyde, 4-aminosalicylic aldehyde, and 5, aminosalicylic aldehyde.

In order to fully understand the preferred dye compositions of this invention, a detail formula is provided for each of the preferred aryl amines and aryl aldehydes. In Table I, each of the preferred aryl amines are listed along with the formula for each, while Table II contains each of the preferred aryl aldehydes and their respective formulas.

TABLE I

| Aryl Amine | Formula |
|---|---|
| p-phenylenediamine | NH₂-C₆H₄-NH₂ |
| N-phenyl-p-phenylenediamine | H₂N-C₆H₄-NH-C₆H₅ |
| p-aminophenol | HO-C₆H₄-NH₂ |
| N,N-bishydroxyethyl-p-phenylenediamine | (CH₂CH₂OH)₂N-C₆H₄-NH₂ |

TABLE II

| Aryl Aldehyde | Formula |
|---|---|
| N,N-dimethyl-4-aminobenzaldehyde | (CH₃)₂N-C₆H₄-CHO |
| N,N-dimethyl-4-aminocinnamaldehyde | (CH₃)₂N-C₆H₄-CH=CHCHO |
| 3,4-dihydroxybenzaldehyde | OHC-C₆H₃(OH)(OH) |
| 4-hydroxybenzaldehyde | OHC-C₆H₄-OH |
| 2,4 dihydroxybenzaldehyde | OHC-C₆H₃(OH)(OH) |
| 4-aminosalicylic aldehyde | OHC-C₆H₃(OH)(NH₂) |
| 5-aminosalicylic aldehyde | OHC-C₆H₃(OH)(NH₂) |

By employing the present invention, a board range of hair colors and color shades is obtained. In this way, natural hair colors can be revitalized or modified and color appearances are enhanced by adding to the surrounding color or by neutralizing unwanted color tints that may have developed on the hair fibers.

By employing the present invention and combining an appropriate aryl alone with particular aryl aldehyde, virtually any color sought is obtained with complete assurance and predictability. In Table III, a representative listing is provided of the different colors that are obtained by combining various aryl amines with various aryl aldehydes. Although not completely exhausted, the combinations detailed in Table III provide a representative sampling of the color range obtainable by employing the present invention.

TABLE III

| AMINE | ALDEHYDE | COLOR |
|---|---|---|
| p-phenylenediamine | N,N-dimethyl-4-aminobenzaldehyde | red-orange |
| N-phenyl-p-phenylenediamine | N,N-dimethyl-4-aminobenzaldehyde | red-violet |
| N-phenyl-p-phenylenediamine | N,N-dimethyl-4-aminocinnamaldehyde | violet-blue |
| p-aminophenol | N,N-dimethyl-4-aminocinnamaldehyde | orange |
| p-aminophenol | N,N-dimethyl-4-aminobenzaldehyde | yellow-orange |
| p-aminophenol | 3,4-dihydroxybenzaldehyde | bright yellow |
| 4-aminosalicylic acid | 3,4-dihydroxybenzaldehyde | yellow-green |
| 4-aminosalicylic acid | N,N-dimethyl-4-aminocinnamaldehyde | orange-red |

In employing the present invention and obtaining the desired, predictable hair coloring, a variety of alternate application procedures can be employed. As a result, the hair dye compositions of the present invention are easily employed, using the most convenient method.

In one application method, the dedired aryl amine is combined with the desired aryl aldehyde along with methyl cellulose, sorbitol, citric acid, panthenol, and water. The entire mixture is applied to the hair and allowed to stand for an extended time period. Then, the hair is shampooed and rinsed, resulting in the precisely desired hair coloring being obtained.

In an alternate procedure, the aryl amine is mixed with methyl cellulose, sorbitol, citric acid, and water and applied to the hair. After standing for a specific time period, the aryl aldehyde is applied as a separate composition along with methyl cellulose, panthenol, and the desired inorganic metal salt. This second solution is allowed to remain on the hair for an extended time period and, once completed, the solution is rinsed off to produce the precisely desired color.

In the third application method, all of the ingredients, except for the inorganic metal salt, are combined and applied to the hair as a paste. This composition is allowed to stand on the hair for an extended time period and then rinsed from the hair. Next, the hair is shampooed with a composition incorporating the inorganic metal salt. The shampoo is then rinsed out of the hair, and the precisely desired color is obtained.

As is apparent from the variety of application methods, the present invention is capable of being used on any desired head of hair using a procedure which is the most convenient to the user. In this way, anyone desiring a predictable, permanent hair coloring is able to obtain any desired hair coloring with assurance that the common prior art difficulties and drawbacks will not be experienced.

In order to attain the desired permanent, long-lasting, non-fading hair coloring using the compositions of the present invention, it has been found that the aryl amine and the aryl aldehyde are preferably prepared as separate solutions and then intermixed, depending upon the desired procedure. In Table IV, the preferred formulation for the aryl amine solution is provided, while Table V lists the preferred formulation for the aryl aldehyde solution.

TABLE IV

| Ingredients | % By Weight Range | % by Weight Preferred |
| --- | --- | --- |
| Methyl Cellulose | 0.1%–10% | 2.00 |
| Sorbitol | 0.05%–5% | 1.00 |
| Aryl Amine | 0.1%–3% | 1.00 |
| Citric Acid | 0.01%–1.0% | 0.10 |
| Water | | q.s. |

TABLE V

| Ingredients | % by Weight Range | % by Weight Preferred |
| --- | --- | --- |
| Methyl Cellulose | 0.1%–10.00% | 2.50 |
| Aryl Aldehyde | 0.1%–3.00% | 0.75 |
| Inorganic Metal Salt | 0.1%–5.00% | 0.50 |
| Panthenol | 0.01%–0.50% | 0.25 |
| Water | | q.s. |

As detailed above, the aryl aldehyde is preferably selected from the group consisting of p-phenylenediamine, N-phenyl-p-phenylenediamine, p-aminophenol, and N,N-bishydroxyethyl-p-phenylenediamine. The preferred aryl aldehyde is selected from the group consisting of N,N-dimethyl-4-aminobenzaldehyde, N-N-dimethyl-4-amino-cinnamaldehyde, 3,4-dihydroxybenzaldehyde, 4-hydroxybenzaldehyde, 2,4-dihydroxybenzaldehyde, 4-aminosalicylic aldehyde and 5-aminosalicylic aldehyde. Finaly, as previously stated, the preferred inorganic metal salt is preferably selected from the group consisting of aluminum chloride, ferric chloride, lithium bromide, manganese chloride, copper chloride, and manganese nitrate.

EXAMPLES

In order to prove the efficacy of the present invention in providing a long-lasting, effective, non-fading, non-light sensitive hair dye composition, the following experiments were conducted. These examples are provided to show the effectiveness of the present invention and are not intended, in any way, to limit the scope of the present invention.

In order to assure uniformity of comparison, each of the following experimental tests were conducted using p-phenylenediamine as the aryl amine, N-N-dimethyl-4-aminobenzaldehyde as the aryl aldehyde, and ferric chloride as the inorganic metal salt. In the first test procedure, the hair dye composition of the present invention was tested as a single, combined hair dye formulation. In conducting this test, the formulation detailed in Tables IV and V were combined to achieve a hair dye composition for application to the test subject.

Once the combined hair dye formulation was achieved, the formulation was applied to white hair and allowed to stand for thirty minutes. Then, the hair was shampooed and rinsed. The result produced a red-orange color which provided a non-fading, permanent hair dye precisely in accordance with the predicted color shown in Table III.

In the next example, the formulation detailed in Table IV was prepared using p-phenylenediamine as the aryl amine, Once prepared, the aryl amine composition was applied to white hair and allowed to stand for five minutes. After the five minutes, the formulation detailed in Table V was applied to the hair and allowed to stand for twenty minutes. Once this time period had lapsed, the hair was rinsed to remove the compositions, revealing the attainment of the predicted red-orange color.

In the final test procedure, the formulations detailed in both Tables IV and V were prepared as a single composition, with the exception of the inorganic metal salt. The formulation obtained was applied as a paste to the hair and allowed to stand for twenty minutes. Next, the hair was rinsed and then shampooed with a shampoo comprising ammonium laureth sulfate, sodium lauryl sulfate, methyl cellulose, and ferric chloride. Once completed, the hair was rinsed and the expected red-orange color was obtained.

In Table VI, a complete formulation is provided for a typical shampoo employable in this invention. Although shampoo formulations of this type are preferred, it is understood that this shampoo formulation is representative of shampoos that may be used and is not intended to limit the present invention.

TABLE VI

| | % by Weight |
| --- | --- |
| Ammonium Lauryl Sulfate | 20.000 |
| Cocamidopropyl Betaine | 2.000 |
| Lauramide DEA | 2.000 |
| Inorganic Metal Salt | 1.000 |
| Sodium Chloride | 0.800 |
| Hydroxylpropyl Methylcellulose | 0.400 |
| Hydrogenated Starch Hydrolysate | 0.400 |
| Polyquaternium-11 | 0.400 |
| Acetamide MEA | 0.300 |
| Floral Apple Fragrance | 0.300 |
| DMDM Hydantoin | 0.100 |
| Panthenol | 0.100 |
| Citric Acid, Anhydrous USP | 0.075 |
| Deionized Water | q.s. |

In each of the foregoing experiments, the resulting dyed hair was tested to determine its ability to resist fading in exposed light, as well as its ability to retain the desired color. Each of the hair samples obtained were simultaneously tested with all results showing each method to be equally effective in providing a long-lasting, non-fading, hair dye composition wich attains a natural dye color using an application method which is easily employed.

By referring to Table VII, the ability of the present invention to achieve dyed hair which resists fading in exposed light, and retains the desired color is clearly shown by the data provided. In these tests, the hair dye compositions of the present invention were employed using the method wherein the hair is first treated with the aryl amine and aryl aldehyde combined and then shampooed with a shampoo incorporating the desired inorganic metal salt.

In conducting these test, the shampoo detailed in Table VI was employed. In addition, in order to prove the efficacy of the present invention and the ability of the hair fiber to resist fading in exposed light using this method, control samples were also tested in the same manner as detailed above, except that hair fibers were shampooed using a shampoo formulation which did not contain any inorganic metal salt.

TABLE VII

| Aldehyde | Amine | Change in Hunter Chromicity Values | |
|---|---|---|---|
| | | No Metal Salt | Metal Salt |
| N,N-dimethyl-4-aminocinnamaldehyde | p-phenylenediamine | 4.96 | 2.25 |
| N,N-dimethyl-4-aminocinnamaldehyde | p-aminophenol | 15.93 | 3.76 |
| N,N-dimethyl-4-aminocinnamaldehyde | N-phenyl-p-phenylenediamine | 3.61 | 2.11 |
| N,N-dimethyl-4-aminobenzaldehyde | p-phenylenediamine | 5.89 | 2.96 |
| N,N-dimethyl-4-aminobenzaldehyde | p-aminophenol | 8.25 | 4.93 |
| N,N-dimethyl-4-aminobenzaldehyde | N-phenyl-p-phenylenediamine | 8.38 | 6.62 |
| 2,4 dihydroxybenzaldehyde | p-phenylenediamine | 5.82 | 3.11 |
| 2,4 dihydroxybenzaldehyde | p-aminophenol | 10.33 | 6.15 |
| 2,4 dihydroxybenzaldehyde | N-phenyl-p-phenylenediamine | 8.48 | 1.72 |

The test results provided in Table VII represent the change in the Hunter Chromicity Values for each of the hair samples tested using different combinations of aryl aldehydes and aryl amines. In determining the change in the Hunter Chromicity value, the following formula was employed:

$$DE = \sqrt{(a_i - a_f)^2 + (b_i - b_f)^2 + (L_i - L_f)^2}$$

where:
i = initial reading
f = exposure for 10 hours in simulated sunlight
L = total reflectance of 0 = black, 100 = white
a = (+) for red; (−) for green
b = (+) yellow, (−) for blue.

In all of the tests conducted for which the results are provided in Table VII, blended gray hair was employed and all values were determined by the average of triplicate measurements. Furthermore, all of the measurements were made using a Spectrogard II system available from Pacific Instruments.

As is apparent from the results obtained, the hair dye compositions of the present invention provide substantially improved results, imparting to the hair a long lasting, stable, and effective dye which is able to withstand extended exposure to light without substantial fading.

It will thus be seen that the objects set forth above, among those made apparent from the preceding description, are efficiently attained and, since certain changes may be made in carrying out the above method, as well as in the composition set forth above, without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Particularly, it is to be understood that in said claims, ingredients or compounds recited in the singular are intended to include compatible mixtures of such ingredients wherever the sense permits.

Having described our invention, what we claim is new and desired to secure by Letters Patent is:

1. A hair dye composition for imparting a stable, effective and longlasting coloring to the hair said composition comprising
    A. between about 0.1% and 20% by weight of methylcellulose;
    B. between about 0.05% and 5% by weight of sorbitol;
    C. between about 0.1% and 3% by weight of an aryl amine selected from the group consisting of p-phenylenediamine, N-phenyl-p-phenylenediamine, p-aminophenol, and N,N-bishydroxyethyl-p-phenylenediamine;
    D. between about 0.1% and 3% by weight of an aryl aldehyde selected from the group consisting of N,N-dimethyl-4-aminobenzaldehyde, N,N-dimethyl-4-aminocinnamaldehyde, 3,4-dihydroxybenzaldehyde, 4-hydroxybenzaldehyde, 2,4-dihydroxybenzaldehyde, 4-aminosalicylic aldehyde, and 5-aminosalicylic aldehyde;
    E. between about 0.1% and 5% by weight of an inorganic metal salt having a valence between +1 and +3 selected from the group consisting of aluminum chloride, ferric chloride, lithium bromide, manganese chloride, copper chloride and manganese nitrate;
    F. between about 0.01% and 1.0% by weight of citric acid;
    G. between about 0.01% and 0.50% by weight of panthenol; and
    H. water forming the balance.

2. The hair dye composition defined in claim 1, wherein said composition is further defined as comprising
    A. about 4.5% by weight of methyl cellulose;
    B. about 1.0% by weight of sorbitol;
    about 1.0% by weight of the aryl amine;
    D. about 0.75% by weight of the aryl aldehyde;
    E. about 0.50% by weight of the inorganic metal salt;
    F. about 0.10% by weight of citric acid; and
    G. about 0.25% by weight of panthenol.

3. A method for imparting a stable, effective and long-lasting coloring to hair fibers comprising the steps of
   A. preparing an aryl amine bearing solution comprising
      a. between about 0.1% and 10% by weight of methyl cellulose,
      b. between about 0.05% and 3% by weight of sorbitol,
      c. between about 0.1% and 3% by weight of an aryl amine selected from the group consisting of p-phenylenediamine, N-phenyl-p-phenylenediamine, p-aminophenol and N,N-bishydroxyethyl-p-phenylenediamine,
      d. between about 0.01% and 1% by weight of citric acid, and
      e. water forming the balance;
   B. applying the aryl amine bearing solution to the hair to be dyed;
   C. preparing an aryl aldehyde bearing solution comprising
      a. between about 0.1% and 10% by weight of methyl cellulose,
      b. between about 0.1% and 3% by weight of an aryl aldehyde selected from the group consisting of N,N-dimethyl-4-aminobenzaldehyde, N,N-dimethyl-4-aminocinnamaldehyde, 3,4-dihydroxybenzaldehyde, 4-hydroxybenzaldehyde, 2,4-dihydroxybenzaldehyde, 4-aminosalicylic aldehyde and 5-aminosalicylic aldehyde,
      c. between about 0.1% and 5% by weight of an inorganic metal salt having a valence between +1 and +3 selected from the group consisting of aluminum chloride, ferric chloride, lithium bromide, manganese chloride, copper chloride and manganese nitrate,
      d. between about 0.01% and 0.50% by weight of panthenol, and
      e. water forming the balance;
   D. applying the aryl aldehyde bearing solution to the hair fiber for being intermixed with the aryl amine bearing solution;
   E. allowing the combined solutions to remain on the hair for and extended time period; and
   F. rinsing the solutions from the hair after the desired exposure time to produce the precisely desired coloring.

4. The method of claim 3, wherein the aryl amine bearing solution was allowed to remain on the hair for about five minutes before applying the aryl aldehyde bearing solution to the hair.

5. The method defined in claim 4, wherein the combined aryl amine and aryl aldehyde solutions are allowed to remain on the hair for between about 20 to 30 minutes before rinsing the hair.

6. A method for imparting a stable, effective and long-lasting coloring to the hair comprising the steps of
   A. preparing a hair dye composition comprising
      a. between about 0.1% and 20% by weight of methyl cellulose,
      b. between about 0.05% and 5% by weight of sorbitol,
      c. between about 0.1% and 3% by weight of an aryl amine selected from the group consisting of p-phenylenediamine, N-phenyl-p-phenylenediamine, p-aminophenol and N,N-bishydroxyethyl-phenylenediamine,
      d. between about 0.1% and 3% by weight of an aryl aldehyde selected from the group consisting of N,N-dimethyl-4-aminobenzaldehyde, N,N-dimethyl-4-aminocinnanaldehyde, 3,4-dihydroxybenzaldehyde, 4-hydroxybenzaldehyde, 2,4-dihydroxybenxzaldehyde, 4-aminosalicylic aldehyde and 5-aminosalicylic aldehyde,
      e. between about 0.01% and 0.5% by weight of panthenol,
      f. between about 0.01% and 1.0% by weight of citric acid, and
      g. water forming the balance;
   B. applying the composition to the hair as a paste;
   C. allowing the composition to remain on the hair for an extended time period;
   D. rinsing the paste composition from the hair;
   E. shampooing the hair with a shampoo comprising an inorganic metal salt having a valence between +1 and +3 selected from the group consisting of aluminum chloride, ferric chloride, lithium bromide, manganese chloride, copper chloride and manganese nitrate; and
   F. rinsing the shampoo from the hair to obtain the precisely desired long-lasting color in the hair.

7. The method defined in claim 6, wherein the hair dye composition is allowed to remain on the hair for about 20 minutes prior to shampooing the hair.

8. The method defined in claim 6, wherein the shampoo is further defined as comprising ammonium laureth sulfate, sodium lauryl sulfate and methyl cellulose.

9. The method in claim 6, wherein the shampoo is further defined as comprising
   a. about 20% by weight of ammonium lauryl sulfate,
   b. about 2.0% by weight of cocamidopropyl betaine,
   c. about 2.0% by weight of lauramide DEA,
   d. about 1.0% by weight of an inorganic metal salt,
   e. about 0.80% by weight of sodium chloride,
   f. about 0.40% by weight of hydroxypropyl methylcellulose,
   g. about 0.40% by weight of hydrogenated starch hydrolysate,
   h. about 0.40% by weight of polyquaternium-11,
   i. about 0.30% by weight of acetamide MEA,
   j. about 0.30% by weight of floral apple fragrance
   k. about 0.10% by weight of DMDM hydantoin,
   l. about 0.10% by weight of panthenol,
   m. about 0.075% by weight of citric acid, anhydrous USP, and
   n. deionized water forming the balance.

* * * * *